US010441515B2

(12) United States Patent
Akinbobola et al.

(10) Patent No.: US 10,441,515 B2
(45) Date of Patent: *Oct. 15, 2019

(54) BEAUTY CARE PRODUCT

(71) Applicant: Noxell Corporation, Hunt Valley, MD (US)

(72) Inventors: Victor Akinbobola, West Chester, OH (US); Alton Lloyd Finley, Cincinnati, OH (US); Matthew David Joseph, Pittsford, NY (US); Christopher Robert Kopulos, Cincinnati, OH (US); Nicholas Arthur Ruebusch, Ft. Thomas, KY (US)

(73) Assignee: Noxell Corporation, Hunt Valley, MD (US)

( * ) Notice: Subject to any disclaimer, the term of this patent is extended or adjusted under 35 U.S.C. 154(b) by 634 days.

This patent is subject to a terminal disclaimer.

(21) Appl. No.: 15/042,288

(22) Filed: Feb. 12, 2016

(65) Prior Publication Data
US 2016/0158124 A1    Jun. 9, 2016

Related U.S. Application Data
(62) Division of application No. 14/265,722, filed on Apr. 30, 2014, now Pat. No. 9,289,045.
(Continued)

(30) Foreign Application Priority Data
Oct. 31, 2013 (EP) ..................................... 13191005

(51) Int. Cl.
*A61K 8/22* (2006.01)
*A45D 19/02* (2006.01)
(Continued)

(52) U.S. Cl.
CPC .................. *A61K 8/22* (2013.01); *A45D 7/04* (2013.01); *A45D 19/02* (2013.01); *A61K 8/0204* (2013.01);
(Continued)

(58) Field of Classification Search
CPC ................ A45D 7/04; A45D 2019/025; A45D 2019/0066; A45D 2007/001; A45D 2200/058; A45D 2200/25; A61K 8/22
See application file for complete search history.

(56) References Cited

U.S. PATENT DOCUMENTS

| 4,946,053 A | 8/1990 | Conrad |
| 6,077,579 A | 6/2000 | De LaForcade |

(Continued)

FOREIGN PATENT DOCUMENTS

| CN | 1585610 A | 2/2005 |
| EP | 1593605 A1 | 11/2005 |

(Continued)

OTHER PUBLICATIONS

"Chinese Application Serial No. 201480022427.X, Response filed Dec. 27, 2017 to Office Action dated Mar. 23, 2017", (w/English Translation of Claims), 9 pgs.
(Continued)

*Primary Examiner* — Cris L. Rodriguez
*Assistant Examiner* — Brianne E Kalach
(74) *Attorney, Agent, or Firm* — Schwegman Lundberg & Woessner, P.A.

(57) ABSTRACT

A beauty care product comprising a sealable plastic container, a sealing means and a beauty care component is provided, wherein the container of which is resistant to random, uncontrolled deformation under a substantial pressure differential between the environment and inside the container, yet having an affordable cost of manufacture
(Continued)

and/or being appealing to the consumer. A kit comprising said product thereof, a method of manufacturing said product, and a method of using said product for application onto skin and/or hair are also provided.

14 Claims, 2 Drawing Sheets

Related U.S. Application Data

(60) Provisional application No. 61/820,346, filed on May 7, 2013.

(51) Int. Cl.
  *A45D 7/04* (2006.01)
  *A61K 8/02* (2006.01)
  *A61Q 5/10* (2006.01)
  *B65D 1/32* (2006.01)
  *B65D 1/02* (2006.01)
  *B65D 79/00* (2006.01)
  *A61Q 5/08* (2006.01)
  *A45D 19/00* (2006.01)
  *A45D 7/00* (2006.01)

(52) U.S. Cl.
  CPC ............ *A61Q 5/08* (2013.01); *A61Q 5/10* (2013.01); *B65D 1/023* (2013.01); *B65D 1/0207* (2013.01); *B65D 1/0223* (2013.01); *B65D 1/32* (2013.01); *B65D 79/005* (2013.01); *A45D 2007/001* (2013.01); *A45D 2019/0066* (2013.01); *A45D 2200/058* (2013.01); *A45D 2200/25* (2013.01); *A61K 2800/87* (2013.01); *B65D 2501/0081* (2013.01)

(56) References Cited

U.S. PATENT DOCUMENTS

| | | | |
|---|---|---|---|
| 6,637,613 B2 | 10/2003 | Shimada | |
| 7,163,123 B2 | 1/2007 | Bezek | |
| 7,425,220 B2 | 9/2008 | Barrass et al. | |
| D653,120 S | 1/2012 | Dombrowski | |
| 9,289,045 B2 | 3/2016 | Akinbobola et al. | |
| 2005/0067369 A1 | 3/2005 | Trude | |
| 2006/0054635 A1 | 3/2006 | Iwahashi et al. | |
| 2008/0257856 A1 | 10/2008 | Melrose | |
| 2009/0050171 A1 | 2/2009 | Barrass et al. | |
| 2009/0095702 A1 | 4/2009 | Ungrady | |
| 2010/0126523 A1* | 5/2010 | Fujinuma | A45D 19/02 132/221 |
| 2012/0175338 A1 | 7/2012 | Castillo Higareda et al. | |
| 2013/0292355 A1 | 11/2013 | Lausted | |
| 2013/0313217 A1 | 11/2013 | Yamamoto | |

FOREIGN PATENT DOCUMENTS

| | | |
|---|---|---|
| EP | 2087878 A1 | 8/2009 |
| JP | 2003-276719 A | 10/2003 |
| JP | 2008-291020 A | 12/2008 |
| JP | 4357183 B2 | 11/2009 |
| JP | 2010179063 A | 8/2010 |
| JP | 2016-525987 A | 9/2016 |
| WO | WO-2004071887 A1 | 8/2004 |
| WO | WO-2005047121 A2 | 5/2005 |
| WO | WO-2014182511 A1 | 11/2014 |

OTHER PUBLICATIONS

"Chinese Application Serial No. 201480022427.X, Office Action dated Jan. 15, 2018", Without English Translation, 6 pgs.
"Chinese Application Serial No. 201480022427.X, Response filed Mar. 28, 2018 to Office Action dated Jan. 15, 2018", w/ English Claims, 10 pgs.
"Japanese Application Serial No. 2016-512945, Examiners Decision of Final Refusal dated Jul. 11, 2017". (w/ English Translation), 6 pgs.
"U.S. Appl. No. 14/265,722, Notice of Allowance dated Nov. 16, 2015", 8 pgs.
"U.S. Appl. No. 14/265,722, Response filed Sep. 8, 2015 to Restriction Requirement dated Jul. 8, 2015", 7 pgs.
"U.S. Appl. No. 14/265,722, Restriction Requirement dated Jul. 8, 2015", 7 pgs.
"European Application Serial No. 13191005.1, Response filed Mar. 26, 2015 to Extended European Search Report dated Apr. 22, 2014", 6 pgs.
"European Application Serial No. 13191005.1, Extended European Search Report dated Apr. 22, 2014", 7 pgs.
"International Application Serial No. PCT/US2014/035976, International Preliminary Report on Patentability dated Nov. 19, 2015", 8 pgs.
"International Application Serial No. PCT/US2014/035976, International Search Report dated Jul. 10, 2014", 3 pgs.
"International Application Serial No. PCT/US2014/035976, Written Opinion dated Jul. 10, 2014", 6 pgs.
"Japanese Application Serial No. 2016-512945, Office Action dated Nov. 8, 2016", (w/ English Translation), 4 pgs.
"Chinese Application Serial No. 201480022427.X, Office Action dated Mar. 23, 2017", (w/ English Translation), 13 pgs.
"Japanese Application Serial No. 2016-512945, Written Argument and Amendment filed Apr. 24, 2017 to Office Action dated Nov. 8, 2016", (w/English Translation), 15 pgs.
"Chinese Application Serial No. 201480022427.X, Office Action dated Apr. 18, 2018", w/ English translation, 6 pgs.
"Chinese Application Serial No. 201480022427.X, Response filed Jun. 20, 2018 to Office Action dated Apr. 18, 2018", w/ English Claims, 10 pgs.

* cited by examiner

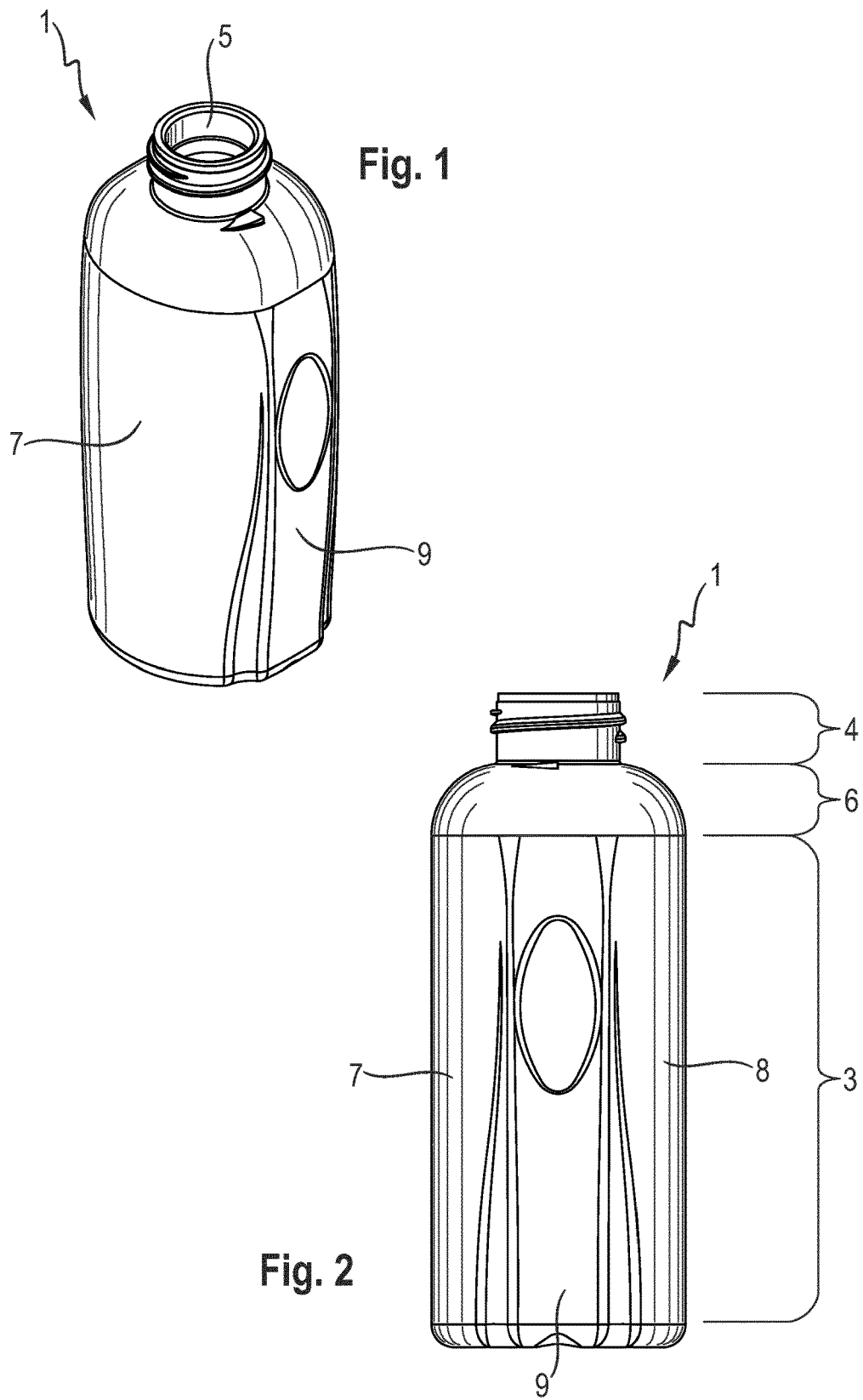

BEAUTY CARE PRODUCT

FIELD OF THE INVENTION

The present invention relates to a beauty care product comprising a sealable plastic container, a sealing means and a beauty care component; to a kit comprising said product thereof; to a method of manufacturing said product; and to a method of using said product for application onto skin and/or hair. The present invention provides a product, the container of which is resistant to random, uncontrolled deformation under a substantial pressure differential between the environment and inside the container, yet having an affordable cost of manufacture and/or being appealing to the consumer.

BACKGROUND OF THE INVENTION

Beauty care compositions, particularly hair coloring and/or bleaching compositions and/or heat-generating cosmetic compositions, may involve reactive chemistry, as they comprise ingredients undergoing a chemical reaction when placed in contact with each other. For example, oxidative hair color compositions comprise a primary precursor (also called coupler), a secondary precursor (also called developer) and an oxidizing agent such as ammonia. When mixed together, a chemical reaction occurs so that a dye is formed.

Such chemical reaction is wanted upon application onto hair, but not before. For avoiding the chemical reaction to occur prematurely such as upon manufacture and/or upon storage, these ingredients are usually comprised within different components, such as a first component (also called a tint) comprising the primary precursor and a second component (also called the developer) comprising the secondary precursor. These components may be sold as a kit and be packaged individually in any suitable packaging, wherein these kits comprise at least two components to be mixed extemporaneously i.e. shortly before application onto hair.

Professional hairdressers are usually mixing the different components using a bowl and a spatula. Untrained users such as consumers coloring their hair by themselves are not willing to mix the components in a bowl, as the mixture obtained may lack homogeneity, leading afterwards to an uneven hair coloration and also because such process is uneasy to achieve, and may lead to staining the area where the mixing is taking place e.g. the sink, the bathtub, and/or the floor.

For avoiding such drawbacks, hair coloring and/or bleaching kits are usually provided with at least one squeezable plastic container comprising about 70% or less of a component upon storage. At least one of the other components is poured into the container, mixed together with its content, and the resulting hair coloring and/or bleaching composition is applied onto hair by squeezing the plastic container.

Such type of containers while being convenient upon use, have shown drawbacks upon storage. Indeed, they usually comprise relatively thin panels in order to be squeezable i.e. deformable upon application of localized pressure onto the container by hand without excessive force. However, as these containers are filled with about 70% or less of a component, there is a substantial residual volume filled with gas e.g. ambient air at the place of manufacture. Upon certain circumstances such as a change of temperature and/or a change of altitude, there may have a significant pressure differential between the environment and inside the container. Such differential often leads to an uncontrolled, random deformation of the container. This is unwanted as the container may not be appealing to the consumer, may look defect and/or may even induce the leaking of its content and/or its breakage.

Different solutions have been provided for avoiding these drawbacks. For example, containers comprising thicker labels and/or labels made of more rigid plastics have been provided. These containers require however an increased force for being squeezed, which is inconvenient upon use by the consumer. Containers having pressure-regulating means have also been provided. Such means are usually sophisticated and therefore expensive to be manufactured. It also usually requires at least one additional process step for affixing them onto the container and/or the sealing means. This drives the cost of manufacture up, and impacts negatively on the price of sale of the hair coloring and/or bleaching products and/or kits.

There is a desirable need therefore of providing a hair coloring and/or bleaching product comprising a squeezable plastic container containing upon storage about 70% or less of a hair coloring and/or bleaching component, which is resistant to random, uncontrolled deformation under a substantial pressure differential between the environment and inside the container. There is also the desirable need for providing a hair coloring and/or bleaching product comprising a squeezable plastic container being resistant to uncontrolled deformation, which has an affordable cost of manufacture. There is also the desirable need for providing a hair coloring and/or bleaching product comprising a squeezable plastic container being resistant to uncontrolled deformation, which is appealing to the consumer yet easy to use.

SUMMARY OF THE INVENTION

In one aspect, the present invention relates to a beauty care product comprising:
(a) a sealable plastic container 1 comprising a base section 2, a body section 3, and a neck section 4 forming an aperture 5; said sections delimiting an inner reservoir;
(b) a sealing means, affixed onto the neck section 4 of the container 1;
(c) a beauty care component, contained within the reservoir of the container 1;
wherein the reservoir comprises upon storage no more than about 70% of the component by total volume of the reservoir, the remaining volume being filled with gas; wherein the body section 3 is four-paneled and comprises a non-collapsible squeezable front panel 7, two symmetrical collapsible side panels 9 and 9a and a non-collapsible squeezable back panel 8; wherein the ratio of the average thicknesses between front and/or back panels 7,8 and the side panels 9,9a is at least 2:1. In at least one embodiment, the side panels 9,9a are temporarily deformable in response to a substantial pressure differential between the environment and inside the reservoir of the container 1.

In a second aspect, the present invention relates to a beauty care kit comprising said product, and at least one additional product. In a third aspect, the present invention relates to a method for manufacturing said product. In a fourth aspect, the present invention relates to a method of using said product for application onto hair and/or skin.

BRIEF DESCRIPTION OF THE DRAWINGS

FIG. 1 is a perspective view from above of the container 1, including the front panel and one of the side panel (right).

FIG. 2 is a front view of the container 1.

DETAILED DESCRIPTION OF THE INVENTION

Figure 3:
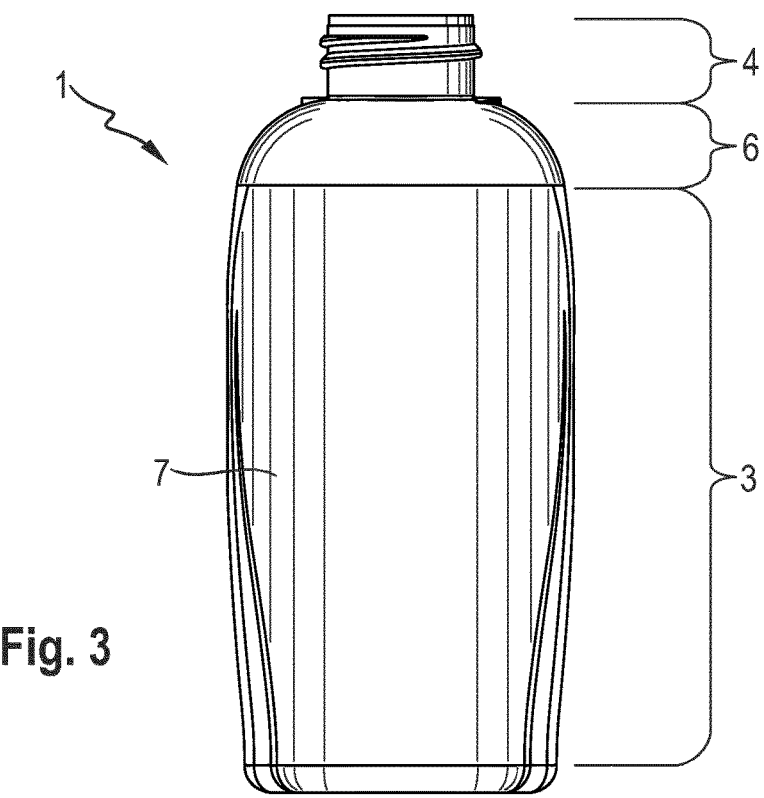
FIG. 3 is a side view (right) of the container 1.
Figure 4:
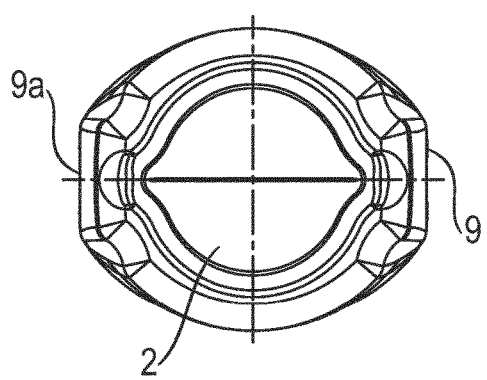
FIG. 4 is a bottom view of the container 1.
Figure 5:
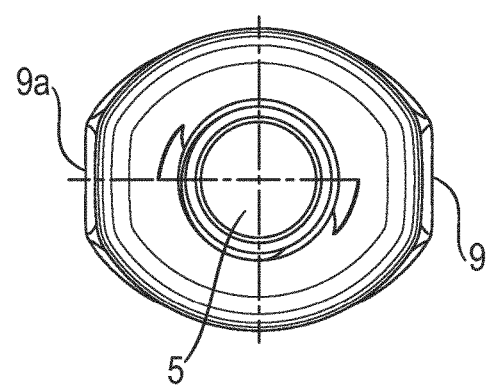
FIG. 5 is a top view of the container 1.

In this document, including in all embodiments of all aspects of the present invention, the following definitions apply unless specifically stated otherwise. All percentages are by weight of the total composition. All ratios are weight ratios. References to 'parts' e.g. a mixture of 1 part X and 3 parts Y, is a ratio by weight. "QS" or "QSP" means sufficient quantity for 100% or for 100 g.+/− indicates the standard deviation. All ranges are inclusive and combinable. The number of significant digits conveys neither a limitation on the indicated amounts nor on the accuracy of the measurements. All numerical amounts are understood to be modified by the word "about". All measurements are understood to be made at 23° C. and at ambient conditions, where "ambient conditions" means at 1 atmosphere (atm) of pressure and at 50% relative humidity. "Relative humidity" refers to the ratio (stated as a percent) of the moisture content of air compared to the saturated moisture level at the same temperature and pressure. Relative humidity can be measured with a hygrometer, in particular with a probe hygrometer from VWR® International. Herein "min" means "minute" or "minutes". Herein "mol" means mole. Herein "g" following a number means "gram" or "grams". All weights as they pertain to listed ingredients are based on the active level and do not include carriers or by-products that may be included in commercially available materials. Herein, "comprising" means that other steps and other ingredients can be in addition. "Comprising" encompasses the terms "consisting of" and "consisting essentially of". The compositions, formulations, methods, uses, kits, and processes of the present invention can comprise, consist of, and consist essentially of the elements and limitations of the invention described herein, as well as any of the additional or optional ingredients, components, steps, or limitations described herein. Embodiments and aspects described herein may comprise or be combinable with elements, features or components of other embodiments and/or aspects despite not being expressly exemplified in combination, unless an incompatibility is stated. "In at least one embodiment" means that one or more embodiments of the present invention has/have the subsequently described feature.

"Molecular weight" or "M.Wt." or "MW" and grammatical equivalents mean the number average molecular weight.

"Water-soluble" refers to any material that is sufficiently soluble in water that when dissolved forms a clear solution to the naked eye at a concentration of 0.1 g of the material in 1 Liter of deionised water at 25° C. and 1 atm pressure. The term "water-insoluble" refers to any material that is not "water-soluble".

"Substantially free from" or "substantially free of" means less than about 1%, or less than 0.8%, or less than 0.5%, or less than 0.3%, or about 0%, by total weight of the composition or formulation.

"Hair" means mammalian keratin fibres including scalp hair, facial hair and body hair. It includes such hair still being attached to a living subject and also hair that has been removed therefrom such as hair swatches and hair on a doll/mannequin. In an embodiment, "hair" means human hair. "Hair shaft" or "hair fibre" means an individual hair strand and may be used interchangeably with the term "hair."

"Cosmetically acceptable" means that the compositions, formulations or components described are suitable for use in contact with human keratinous tissue without undue toxicity, incompatibility, instability, allergic response, and the like. All compositions and formulations described herein which have the purpose of being directly applied to keratinous tissue are limited to those being cosmetically acceptable.

"Derivatives" includes but is not limited to, amide, ether, ester, amino, carboxyl, acetyl, acid, salt and/or alcohol derivatives of a given compound. In at least one embodiment, "derivatives thereof" means the amide, ether, ester, amino, carboxyl, acetyl, acid, salt and alcohol derivatives.

"Monomer" means a discrete, non-polymerised chemical moiety capable of undergoing polymerisation in the presence of an initiator or any suitable reaction that creates a macromolecule e.g. such as polycondensation, polyaddition, anionic or cationic polymerization. "Unit" means a monomer that has already been polymerised i.e. is part of a polymer.

"Polymer" means a chemical formed from the polymerisation of two or more monomers. The term "polymer" shall include all materials made by the polymerisation of monomers as well as natural polymers. Polymers made from only one type of monomer are called homopolymers. Herein, a polymer comprises at least two monomers. Polymers made from two or more different types of monomers are called copolymers. The distribution of the different monomers can be random, alternating or block-wise (i.e. block copolymer). The term "polymer" used herein includes any type of polymer including homopolymers and copolymers.

"Kit" means a package comprising a plurality of components. "Kit" may be referred to as "kit-of-parts". An example of a kit is, for example, a first composition and a separately packaged second composition and optionally application instructions.

As used herein, when describing the container according to the present invention, the expressions "bottom" and "top" are relative to the orientation of the product when resting onto a surface so that the base section of the container (also called bottom section) is orientated toward the bottom of the product and the neck section and sealing means are orientated toward the top of product. Likewise, the expressions "vertical/vertically" and "horizontal/horizontally" are relative to the orientation of the product when resting onto a surface, said surface being horizontal.

As used herein, when describing the panels forming the body section of the container, "front", "back" and "side" are relative to the panel onto which the front label is attached, said front label being the label displaying information about the product to be seen first by the consumer when standing on the supermarket shelf, including, but not limited to, the brand name, logo, slogan, illustrations and/or pictures, information such as the container size, etc.

As a used herein, "beauty care products" means any products being suitable for application onto keratin substrates, including hair, skin, eyebrows, eyelashes, lips, and nails. Beauty care products may include personal care products, make-up products, shave care products and hair care products. Personal care products may include personal and/or facial cleansing products. Make-up products may include mascaras, foundations and enamels. Hair care products may include shampoos, conditioning compositions, styling compositions and hair color compositions.

In a first aspect, the present invention relates to a product comprising a sealable plastic container 1, said container 1 comprising a base section 2, a body section 3, and a neck section 4. The base section 2 allows the container 1 to rest onto a surface, e.g. a supermarket shelf and/or on the bathtub or sink contours. The neck section 4 forms an aperture 5, suitable for pouring a liquid into and/or out of the container 1. The container 1 may also contain a shoulder section 6, joining the body section 3 to the neck section 4.

The base section 2, the body section 3, the neck section 4, and optionally the shoulder section 6 delimit an inner reservoir (not shown). This reservoir comprises a total volume of from about 20 ml to about 1500 ml, alternatively from about 50 ml to about 1000 ml, alternatively from about 75 ml to about 500 ml, alternatively from about 100 ml to about 250 ml, alternatively from about 160 ml to about 170 ml.

A beauty care component (not shown), particularly a hair coloring and/or bleaching component, as described hereinafter, is contained within the reservoir. The reservoir comprises upon storage no more than about 70%, no more than about 50%, alternatively from about 30% to about 50%, of said component by total volume of the reservoir. In another embodiment, the reservoir comprises upon storage less than about 30% and/or at least about 5% of said component by total volume of the reservoir. In still another embodiment, the reservoir (container) is substantially free of any component upon storage.

After filling and sealing, as the inner reservoir is not filled entirely with said component, the reservoir is left with a remaining volume. In a preferred embodiment, said remaining volume is filled with a gas. The gas may be selected from oxygen, nitrogen, carbon dioxide, ambient air, and mixtures thereof; alternatively a gas being ambient air; alternatively a gas being ambient air at a pressure from about 70 kPa to about 101 kPa; alternatively a gas being ambient air at a pressure from about 70 kPa to about 101 kPa and at temperature of from about 15° C. to about 45° C. In at least one embodiment, the remaining volume of the reservoir is filled with ambient air. As used herein, "ambient air" means the ambient air at the time of manufacture of the product, particularly the time at which the container 1 is filled with the component, and subsequently sealed. Without wishing to be bound by any theory, it is believed that, because the reservoir of the container 1 comprises upon manufacture and/or storage a remaining volume filled with a gas at a certain pressure and temperature, this container 1 may be subject to deformation forces, such as extension and/or collapsible forces, whenever a substantial pressure differential between the environment and the reservoir remaining volume occurs. As used herein, "a substantial pressure differential" means a difference of pressure of from about 0.01 kPa to about 30 kPa between the environment and the reservoir remaining volume. Such pressure differential may be induced by a change of temperature inside the reservoir and/or a change of atmospheric pressure in the environment, e.g. because of a change of altitude.

The body section 3 is four-panelled. It comprises a front panel 7, a back panel 8, and two side panels 9 and 9a. These panels are substantially vertical.

The front and back panels 7,8 are non-collapsible and squeezable panels. As used herein, "non-collapsible" means that these panels are not prone to a passive deformation when the container 1 is subject to a substantial pressure differential. As used herein, "squeezable" means that these panels are prone to an active deformation when subject to a substantial force e.g. a force of at least 0.113 Joules (1 in-lb), alternatively from about 0.113 Joules (1 in-lb) to about 4.519 Joules (40 in-lb), alternatively from about 1.130 Joules (10 in-lb) to about 3.390 Joules (30 in-lb), exerted locally onto these panels, preferably a force exerted by the consumer hand. At least one of the front and back panels 7,8 may be functional panels, alternatively the front panel 7 may be a functional panel or both panels 7 and 8 may be functional panels. As used herein, "functional" means that the panels are the support for the labels, comprising various information including, but not limited to, the brand name, logo, slogan, illustrations and/or pictures, information such as the container size, ingredient list, and/or regulatory requirements. The front and/or the back panels 7/8 may have an average thickness of from about 0.50 mm to about 3 mm, alternatively from about 0.50 mm to about 1.5 mm, alternatively from about 0.55 mm to about 1.15 mm. The front and back panels 7,8 may have substantially the same average thickness, alternatively an average thickness differing from about +/−10%, alternatively from about +/−5%, alternatively from about +/−1%.

Thickness can be measured using a calliper device. Average thickness may be measured by taking at least 10 measurements approximately evenly distributed across the area of the panel and then calculating the mean thickness i.e. average thickness, which is measured in millimeters i.e. mm. In at least one embodiment, the average thickness has a standard deviation of less than about +/−10%, or less than about +/−5%, or less than about +/−1%.

The side panels 9 and 9a are collapsible panels. As used herein, "collapsible" means that these panels are prone to a passive deformation when the container is subject to a substantial pressure differential. In at least one embodiment, "substantial pressure differential" means a pressure differential of at least 2%, or at least 5%, or at least 10%, or at least 20% measured in kPa. Preferably, the side panels 9 and 9a are collapsible substantially over their entire surface. In a preferred embodiment, these panels are not intended to be squeezable/squeezed. These panels may be non-functional panels, i.e. these panels may not be the support of any label. The side panels 9 and 9a may have an average thickness of from about 0.25 mm to about 1.5 mm, alternatively from about 0.25 mm to about 0.55 mm. Both side panels 9 and 9a may have substantially the same average thickness, alternatively an average thickness differing from about +/−10%, alternatively from about +/−5%, alternatively from about +/−1%.

In order for the front and back labels 7,8 and the side labels 9,9a to exhibit different properties vis-à-vis collapsibility and squeezability under normal conditions of use, and particularly for obtaining a container having non-collapsible, squeezable front and back panels 7,8 and collapsible side panels 9,9a, the inventors have found that these panels should exhibit a specific differential of average thicknesses. The ratio of the average thicknesses between the front and/or back panels 7,8 and the side panels 9,9a is at least about 2:1, alternatively from about 2:1 to about 5:1, alternatively from about 2:1 to about 3:1, alternatively from about 2:1 to about 2.5:1. Average thickness is measured in millimeters i.e. mm, and thus the ratio of average thickness refers to mm.

In at least one embodiment, the body section 3 is an extended hollow body section. In a preferred embodiment, the body section 3 has a non-cylindrical, non-rectangular and non-squared cross-sectional shape (horizontal cross-section at half height). The body section 3 may have an overall elliptical cross-sectional shape, with the tangents at the panel edges between the side panel 9,9a and the front and/or the back panels 7,8 forming an angle of more than 90° and less than 180°, alternatively from about 100° to about 150°, alternatively from about 110° to about 140°.

In at least one embodiment, the front and/or back panels 7,8 are substantially non-planar relative to a horizontal plane, preferably they are substantially convex in shape relative to a horizontal plane. The front and/or back panels 7,8 may have a radius from about 10 mm to about 40 mm, alternatively from about 10 mm to less than about 20 mm, alternatively from about 20 mm to less than about 30 mm, alternatively from about 30 mm to about 40 mm. The front and/or back panels 7,8 may also be substantially planar relative to a vertical plane.

In at least one embodiment, the side panels 9,9a are substantially non-planar relative to a horizontal plane, preferably they are substantially concave in shape relative to a horizontal plane. The side panels 9,9a may have a radius from about 10 mm to about 55 mm, alternatively from about 10 mm to less than about 20 mm, alternatively from about 20 mm to less than about 30 mm, alternatively from about 40 mm to less than about 55 mm. The side panels 9,9a may also be substantially planar relative to a vertical plane.

In at least one embodiment, the sealable plastic container 1 has a substantially symmetrical shape relative to an axis formed by the center of the aperture and the center of the bottom base section 2.

The container 1 may have a width of from about 20 mm to about 105 mm, alternatively from about 20 mm to about 30 mm, alternatively from about 40 mm to about 50 mm, alternatively from about 90 mm to less than about 105 mm. In at least one embodiment, the width is the average width. Average width may be measured by taking at least 10 measurements approximately evenly distributed across and then calculating the mean width i.e. average width, which is measured in millimeters i.e. mm. In at least one embodiment, the average width has a standard deviation of less than about +/−10%, or less than about +/−5%, or less than about +/−1%.

The container 1 may also have a length of from about 20 mm to 80 mm, alternatively from about 20 mm to about 30 mm, alternatively from about 40 mm to about 50 mm, alternatively from about 70 mm to about 80 mm. In at least one embodiment, the length is the average length. Average length may be measured by taking at least 10 measurements approximately evenly distributed across and then calculating the mean length i.e. average length, which is measured in millimeters i.e. mm. In at least one embodiment, the average length has a standard deviation of less than about +/−10%, or less than about +/−5%, or less than about +/−1%.

The container 1 may also have a height of from about 50 mm to about 300 mm, alternatively from about 50 mm to about 70 mm, alternatively from about 100 mm to about 120 mm, alternatively from about 250 mm to about 270 mm, the height being measured from the bottom of the base section 2 to the top of the neck section 4, excluding the sealing means. In at least one embodiment, the height is the average height. Average height may be measured by taking at least 10 measurements approximately evenly distributed across and then calculating the mean height i.e. average height, which is measured in millimeters i.e. mm. In at least one embodiment, the average height has a standard deviation of less than about +/−10%, or less than about +/−5%, or less than about +/−1%.

The container 1 is made of plastics, alternatively of cosmetic-grade plastics. The base section 2, the body section 3, the neck section 4 and optionally the shoulder section 6 may be made of the same plastics. The container 1 may be made of plastics selected from the group consisting of polyethylene terephthalate (PET), polyethylene (PE), high density polyethylene (HDPE), low density polyethylene (LDPE), polyvinyl chloride (PVC), polyvinylidene chloride (PVDC), polypropylene (PP), polystyrene (PS), high-impact polystyrene (HIPS), polyamides (PA) (Nylons), acrylonitrile butadiene styrene (ABS), polyethylene/acrylonitrile butadiene styrene (PE/ABS), polycarbonate (PC), polycarbonate/acrylonitrile butadiene styrene (PC/ABS), polyurethanes (PU), acrylonitrile butadiene styrene (ABS), Celluloid, Cellulose acetate, ethylene-vinyl acetate (EVA), ethylene vinyl alcohol (EVAL), liquid crystal polymer (LCP), polyacetal (POM or Acetal), polyacrylates (Acrylic), polyacrylonitrile (PAN or Acrylonitrile), polyamide-imide (PAI), polyaryletherketone (PAEK or Ketone), polybutadiene (PBD), polybutylene (PB), polybutylene terephthalate (PBT), polycyclohexylene dimethylene terephthalate (PCT), polyhydroxyalkanoates (PHAs), polyketone (PK), polyester, polyethylene (PE) including low density (LDPE) and high density (HDPE) versions, polyetheretherketone (PEEK), polyetherimide (PEI), polyethersulfone (PES), polyethylenechlorinates (PEC), polyimide (PI), polylactic acid (PLA), polymethylpentene (PMP), polyphenylene oxide (PPO), polyphenylene sulfide (PPS), polyphthalamide (PPA), polysulfone (PSU), and mixtures thereof. The container 1 may alternatively be made of plastics selected from polyolefines; alternatively from the group consisiting of high-density polyethylene (HDPE), low density polyethylene (LDPE), polypropylene (PP), polyethylene terephthalate (PET), derivatives thereof, and mixtures thereof; alternatively from plastics being high-density polyethylene (HDPE). Commercially available HDPE are provided by Exxon under the trade name AS55-003. In a preferred embodiment, the container 1 is made of high-density polyethylene and is substantially free of polyethylene tetraphtalate. In at least one embodiment, the container 1 comprises at least about 80%, or at least about 85%, or at least about 90%, or at least about 95% polyethylene.

The product comprises a sealing means (not shown in figures). In at least one embodiment, the sealing means is suitable for impermeably sealing the container 1 upon storage. Any suitable sealing means may be used. The sealing means may be a lid, a cap, an operculum or a nozzle. The sealing means may be permanently- or releasably-affixed onto the neck section 4 of the container 1. Preferably, the sealing means is releasably-affixed onto the neck section 4 of the container 1.

The product may further comprise at least one label (not shown in figures), alternatively two labels, to be affixed onto the container 1. The labels may be selected from front labels and/or back labels. The front label is usually an aesthetical appealing label, showing for example the brand name, logo, slogan, illustrations and/or pictures. The back label is usually informative, showing for example information such as the container size, INCI list, regulatory requirements, and instructions on how to use the product and/or the component. In a preferred embodiment, the front label is affixed to the front panel 7 and/or the back label is affixed onto the back panel 8. The front and/or back panels may be affixed onto their respective panels 7,8 using any suitable means, such as gluing.

The product comprises a beauty care component (not shown in figures). Preferably, the product comprises a hair coloring and/or bleaching component. The component may comprise a source of an oxidizing agent. Any oxidizing agent known in the art may be used. Preferred oxidizing agents are water-soluble peroxygen oxidizing agents. As used herein, "water-soluble" means that in standard conditions at least about 0.1 g, alternatively about 1 g, alternatively about 10 g of the oxidizing agent can be dissolved in 1 liter of deionized water at 25° C. The component may comprise a total amount of oxidizing agent ranging from about 3% to about 12%, by weight of the total component. Suitable water-soluble oxidizing agents include, but are not limited to: inorganic peroxygen materials capable of yielding hydrogen peroxide in an aqueous solution; alternatively hydrogen peroxide, inorganic alkali metal peroxides, organic peroxides, inorganic perhydrate salt bleaching compounds, and mixtures thereof; alternatively hydrogen peroxide, percarbonates, persulphates, and mixtures thereof. In at least one embodiment, the beauty care component comprises hydrogen peroxide ($H_2O_2$). The beauty care component may be a developer composition. The developer composition may be based on any desired formulation chassis, including any commercial product, for example an oil-in-water emulsion. In at least one embodiment, the developer composition comprises from about 6% to about 9% $H_2O_2$ relative to the total weight of the developer composition. In at least one embodiment, the component is a hair coloring and/or hair bleaching component comprising a total amount of oxidizing agent ranging from about 3% to about 12%, by weight of the total component. A commercial example is the Welloxon® Emulsion with respectively about 6% and about 9% $H_2O_2$, marketed by Wella and comprising as INCI ingredients: Water, $H_2O_2$, Cetearyl Alcohol, Ceteareth-25, Salicylic Acid, Phosphoric Acid, Disodium Phosphate, Etidronic Acid.

In a second aspect, the present invention relates to a beauty care kit, preferably a hair coloring and/or bleaching kit. The kit comprises the beauty care product as described hereinbefore. It also comprises at least an additional product, alternatively from about 2 to about 4 additional products, alternatively 2 or 3 additional products. The additional products may be selected from the group consisting of a product comprising a packaged component, a tool, an instruction sheet, or combinations thereof. The packaged component may be selected from a tint component comprising at least one primary precursor, a component comprising at least a secondary precursor, a conditioning component comprising at least one conditioning active ingredient. Said components may be packaged in any suitable packaging, alternatively from a sealable container, optionally sealed with a sealable means; or a sachet. Said tool may be selected from any tool suitable for coloring and/or bleaching hair, alternatively from a comb, a spatula, a brush, a bowl for missing the components. The instruction sheet may comprise any suitable information, e.g. the step sequence, about on how to color and/or bleach hair with said kit. Any of the disclosure in relation to the first aspect is also relevant to and compatible with the second aspect.

In a third aspect, the present invention relates to a process for manufacturing the product as described herein before. The container may be manufacture using any suitable process of manufacture. In a preferred embodiment, the container is manufactured by a process selected from blow molding, compaction plus sintering. compression molding, expandable bead molding, extrusion blow molding, foam molding, injection molding, injection/stretch blow molding, laminating, reaction injection molding, matched mold, matrix molding, plastic moulding, pressure plug assist molding, rotational molding (or rotomolding), transfer molding, thermoforming vacuum forming, vacuum plug assist molding; alternatively from an extrusion process, alternatively by a continuous extrusion blow molding process. Any of the disclosure in relation to the first and second aspects is also relevant to and compatible with the third aspect.

In a fourth aspect, the present invention relates to a method for coloring and/or bleaching hair. The method comprises the steps of:
(a) providing a first product comprising: a sealable plastic container comprising a base section, a body section, and a neck section forming an aperture; said sections delimitating an inner reservoir; a sealing means, affixed onto the neck section of the container; a developer component, contained within the reservoir of the container; wherein the reservoir comprises upon storage no more than about 70% of the component by total volume of the reservoir, the remaining volume being filled with gas; wherein the body section is four-paneled and comprises a non-collapsible squeezable front panel, two symmetrical collapsible side panels and a non-collapsible squeezable back panel; wherein the ratio of the average thicknesses between front and/or back panels and the side panels is at least 2:1;
(b) providing an additional product being a packaged component selected from a tint component comprising at least one primary precursor, a component comprising at least one secondary precursor, or combination thereof;
(c) pouring the additional product into the reservoir remaining volume of the container of the first product;
(d) mixing the developer component homogeneously with the additional product
(e) applying the mixed composition onto hair.

Any of the disclosure in relation to the first, second and third aspects is also relevant to and compatible with the fourth aspect.

EXAMPLE

The following examples are for illustration and not intended to limit the claim scope.

A beauty care product according to the present invention was obtained starting from a commercially available high-density polyethylene (HDPE) provided by Exxon under the tradename AS55-003 and using an extrusion blow molding process.

The sealable plastic container 1 obtained—as shown in FIG. 1—exhibits the following characteristics:
weight (undecorated): 12.0 g+/−1.5 g;
height (overall): 114.45 mm+/−1.52 mm;
width (max): 51 mm+/−1.52 mm;
depth (max): 44.5 mm+/−0.4 mm;
overflow capacity (OFC): 165 mL+/−5 mL;
side panels thickness (average): 0.39 mm
front panel thickness (average): 1.04 mm
back panel thickness (average): 1.04 mm
difference in wall thickness between front and back panel (measured at the center): 0.0 mm+/−0.1 mm;
difference in wall thickness between two symmetrical side panels (measured at the center): 0.0 mm+/−0.1 mm;
ratio of the average thicknesses between front and/or back panels and the side panels: 2.67 mm total volume of the inner reservoir: 165 ml
I dimension (inner diameter of the neck section): 17.02 mm+/−0.12 mm;
T dimension (outside diameter of the neck section): 23.66 mm+/−0.2 mm;
H dimension (height of the neck section) 12.34 mm+/−0.4 mm;

The sealing means is non-vented closure to be screwed onto the screw thread of the neck section of the container.

The beauty care component is a developer component, conventionally used in the field of hair coloring and/or bleaching hair. This developer is Welloxon 6%. The volume of the developer packaged into the container is of about 60 ml, i.e. about 36% of the total volume of the inner reservoir of the container. The remaining volume filled with ambient air at the place of manufacture is therefore of about 64% of the total volume of the inner reservoir.

The beauty care product is manufactured at a place of manufacture wherein the ambient temperature is about 21° C. to about 26° C. and the atmospheric pressure is about 80 kPa to about 84 kPa.

Upon transportation and/or storage, despite some changes of ambient temperature and/or atmospheric pressure, the container shows satisfactory resistance to random, uncontrolled deformation because of the presence of two symmetrical collapsible side panels having a specific average thickness ratio relative to the front and/or back panels.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm"

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A method for coloring and/or bleaching hair, comprising the steps of:
   (a) providing a first product comprising: a sealable plastic container comprising a base section, a body section, and a neck section forming an aperture; said sections delimiting an inner reservoir; a sealing means, affixed onto the neck section of the container; a developer component, contained within the reservoir of the container; wherein the reservoir comprises upon storage no more than about 70% of the component by total volume of the reservoir, the remaining volume being filled with gas; wherein the body section is four-paneled and comprises a non-collapsible squeezable front panel, two symmetrical collapsible side panels and a non-collapsible squeezable back panel; wherein the ratio of the average thicknesses between front and/or back panels and the side panels is at least 2:1;
   (b) providing an additional product being a packaged component selected from a tint component comprising at least one primary precursor, a component comprising at least one secondary precursor, or combination thereof,
   (c) pouring the additional product into the reservoir remaining volume of the container of the first product;
   (d) mixing the developer component homogeneously with the additional product
   (e) applying the mixed composition onto hair.

2. The method according to claim 1, wherein the side panels are temporarily deformable in response to a substantial pressure differential between the environment and inside the reservoir of the container.

3. The method according to claim 1, wherein the front and/or back panels have an average thickness of from about 0.50 mm to about 3 mm.

4. The method according to claim 1, wherein the sides panels have an average thickness of from 0.25 mm to about 1.5 mm.

5. The method according to claim 1, wherein the container further comprises a shoulder section, joining the body section to the neck section.

6. The method according to claim 1, wherein the reservoir has a total volume of from about 20 ml to about 1500 ml.

7. The method according to claim 1, wherein the remaining volume of the reservoir is filled with ambient air.

8. The method according to claim 1, wherein the body section is an extended hollow body section; and wherein the panels are substantially non-planar relative to the horizontal plane.

9. The method according to claim 1, wherein the panels are substantially non-planar relative to the horizontal plane.

10. The method according to claim 1, wherein the container has a width of from about 20 mm to about 105 mm, a length of from about 20 mm to about 80 mm, and a height of from about 50 mm to about 300 mm.

11. The method according to claim 1, wherein the sealing means is releasably-affixed onto the neck section of the container.

12. The method according to claim 1, wherein the container is made of plastics.

13. The method according to claim 1, wherein the container is made of high-density polyethylene.

14. The method according to claim 1, the container is made of high-density polyethylene and is substantially free of polyethylene terephthalate.

* * * * *